US007811775B2

(12) United States Patent
Nasir et al.

(10) Patent No.: US 7,811,775 B2
(45) Date of Patent: Oct. 12, 2010

(54) FLUORESCENCE POLARIZATION-BASED HOMOGENOUS ASSAY FOR AFLATOXINS

(75) Inventors: Mohammad Sarwar Nasir, Grayslake, IL (US); Michael E. Jolley, Round Lake, IL (US)

(73) Assignee: Diachemix LLC, Milwaukee, WI (US)

( * ) Notice: Subject to any disclaimer, the term of this patent is extended or adjusted under 35 U.S.C. 154(b) by 0 days.

(21) Appl. No.: 12/127,350

(22) Filed: May 27, 2008

(65) Prior Publication Data

US 2008/0227221 A1 Sep. 18, 2008

Related U.S. Application Data

(63) Continuation of application No. 09/905,452, filed on Jul. 13, 2001, now abandoned.

(51) Int. Cl.
*G01N 33/53* (2006.01)
(52) U.S. Cl. ............... 435/7.1; 435/7.92; 435/7.93; 435/7.94; 436/164; 436/172; 436/501
(58) Field of Classification Search ............ 435/7.1, 435/7.92–7.94, 254.3, 810, 915, 975; 436/164, 436/172, 501, 518, 546, 547, 548
See application file for complete search history.

(56) References Cited

U.S. PATENT DOCUMENTS

| 4,444,879 | A | | 4/1984 | Foster et al. | |
|---|---|---|---|---|---|
| 4,772,551 | A | | 9/1988 | Hart et al. | |
| 4,835,100 | A | * | 5/1989 | Dixon et al. | 435/7.93 |
| 5,166,078 | A | * | 11/1992 | McMahon et al. | 436/543 |
| 5,171,686 | A | | 12/1992 | Cotty | |
| 5,262,333 | A | | 11/1993 | Heiman et al. | |
| 5,380,825 | A | | 1/1995 | Stenglein et al. | |
| 5,420,016 | A | * | 5/1995 | Boguslaski et al. | 435/12 |
| 5,427,960 | A | | 6/1995 | Wang et al. | |
| 5,741,654 | A | * | 4/1998 | Michel et al. | 435/7.9 |
| 5,976,820 | A | | 11/1999 | Jolley et al. | |
| 6,432,632 | B2 | | 8/2002 | Nakayama et al. | |
| 6,482,601 | B1 | | 11/2002 | Nasir et al. | |
| 6,812,036 | B2 | | 11/2004 | Nasir et al. | |
| 2002/0055180 | A1 | | 5/2002 | Nasir et al. | |
| 2002/0110803 | A1 | | 8/2002 | Dhar et al. | |

FOREIGN PATENT DOCUMENTS

WO 97/19950 A1 6/1997

OTHER PUBLICATIONS

Nasir et al., Fluorescence Polarization: An Anallytical Tool for Immunoassay and Drug Discovery, Combinatorial Chemistry & High Throughput Screening, 1999, 2, pp. 177-190.*
Richard et al., Analysis of Naturally Occurring Mycotoxing in Feedstuffs and Food, J. Anim. Sci. 1993 71: pp. 2563-2574.*
Holladay, Steven David, "Production of specific antibody against aflatoxin M1," Dissertation Abstracts International, vol. 50, No. 10, p. 4298-B (Apr. 1990).

Pestka, et al., "Immunological Assays for Mycotoxin Detection," Food Technology, vol. 49, No. 2, pp. 120-128 (Feb. 1995).
Neely, et al., "Spectral Studies on the Deoxyribonucleic Acid-Aflatoxin B1 System," Biochemistry, vol. 9, pp. 1862-1866 (1970).
Fukal, et al., "Choice of Procedure Conditions for Radioimmunoassay of Aflatoxin," J. Radioanal. Nucl. Chem. Letters, vol. 108, pp. 259-268 (1986).
Holladay, et al., "Evaluation of an indirect enzyme-linked immunosorbent assay for screening antibody against aflatoxins," Am J Vet Res, vol. 52, No. 2, pp. 222-223 (Feb. 1991).
Maragos, et al., "Fluorescence Polarization as a Means for Determination of Fumonisins in Maize," J. Agric. Food Chem., vol. 49, pp. 596-602 (Feb. 2001).
Nasir et al., "Fluorescence Polarization: An Analytical Tool for Immunoassay and Drug Discovery", Combinatorial Chemistry & High Throughput Screening, vol. 2, pp. 177-190 (1999).
Nasir et al., "Development of a Fluorescence Polarization Assay for the Determination of Aflatoxins in Grains," J. Agric. Food Chem., vol. 50, pp. 3116-3121 (2002).
Langone, J., et al., "Aflatoxin B1: Specific Antibodies and Their-Use in Radioimmunoassay," Journal of the American Cancer Institute, vol. 56, No. 3, pp. 591-595 (Mar. 1976).
Sizaret, P., et al., "Detection of Aflatoxins and Related Metabolites by Radioimmunoassay," JNCI, vol. 69, No. 6, pp. 1375-1381 (Dec. 1982).
Whitaker, et al., "Variability Associated with Analytical Methods Used to Measure Aflatoxin in Agricultural Commodities," Journal of AOAC International, vol. 79, No. 2, pp. 476-485 (1996).
Wilson, T., et al., "Use of the Mycosep Multifunctional Cleanup Column for Liquid Chromatographic Determination of Aflatoxins in Agricultural Products," J. Assoc. Off. Anal. Chem., vol. 74, No. 6, pp. 951-956 (1991).
Newberne, P., et al., "Acute and Chronic Effects of Aflatoxin on the Liver of Domestic and Laboratory Animals: A Review," Cancer Research, vol. 29, pp. 236-250 (Jan. 1969).
Trucksess, M., et al., "Immunoaffinity Column Coupled With Solution Fluorometry or Liquid Chromatography Postcolumn Derivatization for Determination of Aflatoxins in Corn, Peanuts, and Peanut Butter: Collaborative Study," J. Assoc. Off. Anal. Chem., vol. 74, No. 1, pp. 81-88 (1991).

(Continued)

*Primary Examiner*—Melanie Yu
*Assistant Examiner*—Gary W Counts
(74) *Attorney, Agent, or Firm*—McDonnell Hoehnen Hulbert & Berghoff LLP

(57) ABSTRACT

A homogeneous assay for determining the aflatoxin content in agricultural products uses the technique of fluorescence polarization. A solvent is used to extract aflatoxins from a sample of the agricultural product. A mixture is prepared by combining the extract with a tracer and with a monoclonal antibody specific for aflatoxin. The tracer is able to bind to the monoclonal antibody to produce a detectable change in fluorescence polarization. The tracer is prepared by conjugating an aflatoxin oxime to a suitable fluorophore. The fluorescence polarization of the mixture is measured. The aflatoxin concentration of the mixture may be calculated using a standard curve obtained by measuring the fluorescence polarization of a series of aflatoxin solutions of known concentration.

16 Claims, 3 Drawing Sheets

OTHER PUBLICATIONS

Wild, C., et al., "Aflatoxin Detected in Human Breast Milk by Immunoassay," Int. J. Cancer, vol. 40, pp. 328-333 (1987).

Trucksess, et al., "Multifunctional Column Coupled with Liquid Chromatography for Determination of Aflatoxins B1, B2, G1, and G2 in Corn, Almonds, Brazil Nuts, Peanuts, and Pistachio Nuts: Collaborative Study," Journal of AOAC International, vol. 77, No. 6, pp. 1512-1521 (1994).

Campbell, T., et al., "Implication of Mycotoxins for Human Health," J. Agr. Food Chem., vol. 22, No. 6, pp. 1006-1015 (1974).

Seitz, L., "Comparison of Methods for Aflatoxin Analysis by High-Pressure Liquid Chromatography," Journal of Chromatography, vol. 104, pp. 81-89 (1975).

Asao, T., et al., "The Structures of Aflatoxins B and G1," Journal of the American Chemical Society, vol. 87, No. 4, pp. 882-886 (Feb. 20, 1965).

Maragos, C., et al., "Fiber-optic Immunosensor for Mycotoxins," Natural Toxins, vol. 7, pp. 371-376 (1999).

Holladay, S.D., "Preparation of Protein Conjugatable Aflatoxin Oxime Derivative from Significantly Reduced Starting Quantities," Veterinary Human Toxicology, vol. 31, No. 6, pp. 526-527 (1989).

* cited by examiner

1

FLUORESCENCE POLARIZATION-BASED HOMOGENOUS ASSAY FOR AFLATOXINS

CROSS-REFERENCE TO RELATED APPLICATIONS

This is a continuation of application Ser. No. 09/905,452, filed Jul. 13, 2001, now abandoned, which application is incorporated herein by reference.

BACKGROUND OF THE INVENTION

1. Field of the Invention

This invention relates to the field of mycotoxin assays. More particularly, this invention relates to a homogeneous assay that uses changes in fluorescence polarization to detect the presence of aflatoxins in agricultural products.

2. Description of Related Art

Aflatoxins are mycotoxins produced by *Aspergillus flavus* molds[1]. Aflatoxins have been known for a long time, but their carcinogenicity was first detected in the late 1960s[4]. Various forms of aflatoxin, including $B_1$, $B_2$, $G_1$, and $G_2$ and many others, have been found in many forms of human foods, such as cereals, grains and peanut products[9,11]. Aflatoxin $B_1$ is the most abundant of all. An exposure to aflatoxins has been associated with an increased incidence of primary hepatocellular carcinoma[7].

Due to their toxicity and carcinogenicity, various analytical methods have been devised to quantitatively determine the amount of aflatoxin in agricultural products[1-4,6,8]. One difficulty with such assays is that aflatoxins are very hydrophobic and therefore very insoluble in aqueous solvents. Thus, mixtures of organic solvent with water have generally been used to extract aflatoxins from samples.

Another difficulty is that most of the common assays, including TLC and HPLC[10], require extended cleanup steps and derivatization after extraction in order to get rid of interfering substances. ELISA methods are relatively faster but are hard to quantify due to various washing steps, liquid transfers and incubation times and cleaning steps.

Accordingly, there is a need for an assay for the determination of aflatoxins in agricultural products that is rapid, simple to apply, and that can yield quantitative results.

SUMMARY OF THE INVENTION

In a first principal aspect, the present invention provides a homogenous assay for the determination of aflatoxins in agricultural products. Aflatoxin is extracted from a sample, and the extract is combined with a tracer and an antibody to provide a mixture. The antibody is specific for aflatoxin. The tracer comprises an aflatoxin oxime conjugated to a fluorophore. The tracer is able to bind to the antibody to produce a detectable change in fluorescence polarization. The fluorescence polarization of the mixture is measured and compared to a standard curve.

In a second principle aspect, the present invention provides an assay kit for the determination of aflatoxins in agricultural products. The assay kit comprises an antibody and a tracer, each in an amount suitable for at least one assay, and suitable packaging. The antibody is specific for aflatoxin. The tracer comprises an aflatoxin oxime conjugated to a fluorophore. The tracer is able to bind to the antibody to produce a detectable change in fluorescence polarization.

DETAILED DESCRIPTION OF THE PREFERRED EMBODIMENTS

Figure 1:
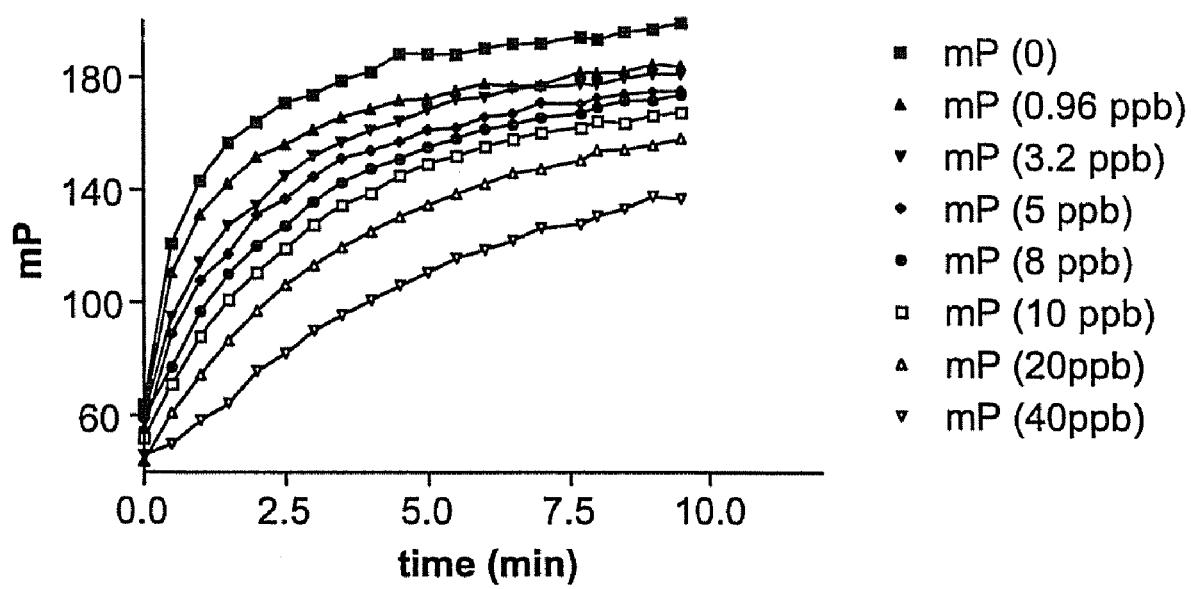
FIG. 1 is a graph showing the change in fluorescence polarization over time for a range of aflatoxin concentrations, in accordance with an embodiment of the present invention.
Figure 2:
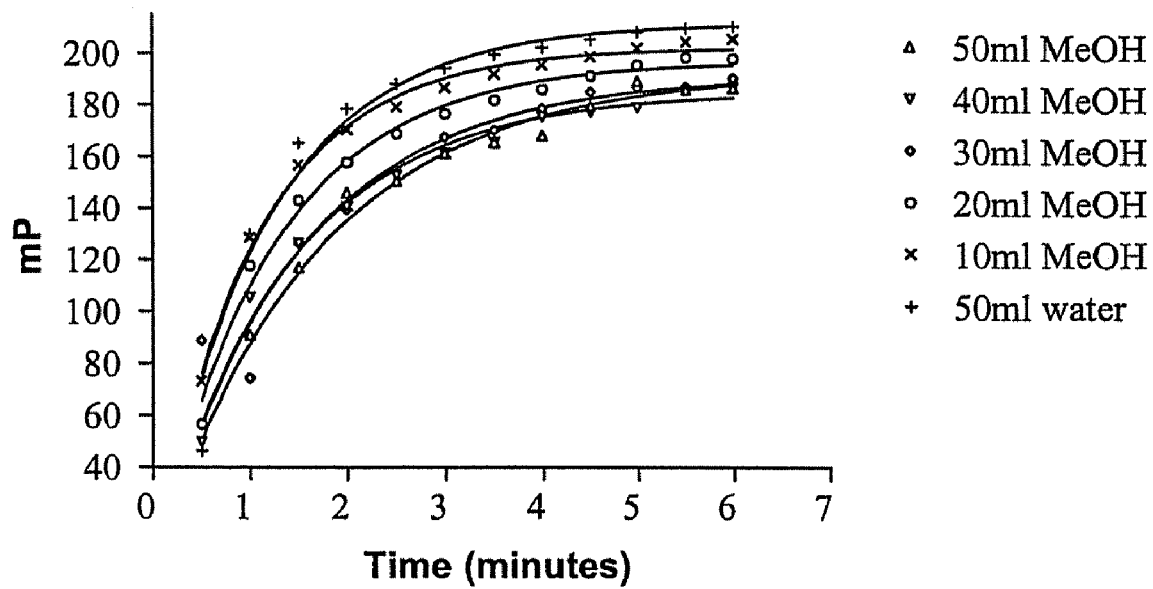
FIG. 2 is a graph showing the change in fluorescence polarization over time for a sample containing no aflatoxin and a range of methanol concentrations, using the data of Table 1, in accordance with an embodiment of the present invention.

The preferred embodiments of the present invention provide a relatively simple homogeneous assay for the determination of aflatoxins in agricultural products that is based on measurements of fluorescence polarization. The technique of fluorescence polarization has been successfully utilized in various assay involving proteins, enzymes, drugs, DNA, hormones, peptides and antibodies.

The principal behind the fluorescence polarization technique is as follows. Fluorescent probes having low molecular weight have low polarization values due to their fast rotation, whereas fluorescent probes with higher molecular weight have higher polarization due to their slower rotation. Thus the polarization value of a fluorophore increases upon binding to a larger molecule. Further information about the fluorescence polarization technique is provided in U.S. Pat. Nos. 5,427,960 and 5,976,820 and in Nasir, M. S. and Jolley, M. E., "Fluorescence Polarization: An analytical tool for Immunoassay and Drug Discovery," *Combinatorial Chemistry & High Throughput Screening*, 1999, 2, 177-190, which references are incorporated herein by reference.

In the present invention, aflatoxin extracted from a sample competes with a fluorescent tracer in the presence of monoclonal antibody, thereby giving rise to a change in fluorescent polarization that is dependent upon the aflatoxin concentration.

The preferred embodiments of the present invention provide a homogeneous assay for aflatoxin that is sensitive, rapid, simple, and inexpensive. It can also be field-portable and yield quantitative results.

1. Materials and Methods

Two different aflatoxin monoclonal antibodies were used in these studies. An aflatoxin monoclonal antibody purchased from Sigma (catalog no. A-9555) was used in initial assay development work, but is was found to have sensitivity to methanol. In later work, a monoclonal antibody, available from Dr. Chris Maragos of the Agricultural Research Unit of the United States Department of Agriculture (Peoria, Ill.), was used because it was found to be stable in methanol. Use of this monoclonal antibody was reported in Chris. M. Maragos and Vicki S. Thompson, "Fiber-optic Immunosensor for Mycotoxins,"*Natural Toxins* 7:371-376 (1999), which is incorporated herein by reference. In addition, many other monoclonal antibodies for aflatoxins are know. See, e.g., U.S. Pat. No. 4,835,100.

Samples of corn that were naturally contaminated with aflatoxins, and samples of aflatoxin-free popcorn were purchased from Trilogy Analytical Laboratory, Inc. (Washington, Mo.). Trilogy also provided an Aflatoxin $B_1/B_2/G_1/G_2$ (7/1/3/1) mixture. Pure Aflatoxin $B_1$ was obtained from Sigma.

Fluorescence polarization measurements were done at room temperature using a single tube Sentry-FP fluorescence polarization instrument (Diachemix Corp.).

2. Preparation of Aflatoxin Tracer

In a 10 ml bottomed flask fitted with a magnetic stirrer and a condenser, Aflatoxin B1 (5 mg, 0.016 mmol, Sigma) and O-carboxymethyl-hydroxylamine-hemihydrochloride (41 mg, 0.19 mmol, Sigma) were mixed with 1.2 ml absolute ethanol. To this solution, 230 μl of a 2 M NaOH solution (0.46 mmol) was added with stirring, and the solution refluxed for 3 hours. The resultant solution we stirred overnight at room temperature, concentrated on a rotary evaporator, and diluted to 1.5 ml with water. Drops of 1 N NaOH were added to adjust the pH to ~9, and the solution was washed with ethyl acetate (using two portions of about 3 ml each), The aqueous layer was acidified with 6 M HCl to a pH ~2, and the resultant mixture was stored at 0° C. in a refrigerator. Some solid precipitated, which was separated and dried. TLC on silica using ethyl acetate:MeOH:NH$_4$OH (32:17:5) gave a major spot at Rf ~0.5 corresponding to the oxime product.

A 20 μl THF solution of (Aflatoxin $B_1$)-O-carboxymethyloxime, prepared as described above, was mixed with 20 μl of dicyclohexycarbodiimide (DDC) in methylene chloride (10 mg/ml) and 200 μl of methylene chloride. After 2-3 minutes, a 20 μl THF solution of fluoresceinamine (isomer 2, 10 mg/ml) was added. The reaction was performed overnight at room temperature. As a control, the same reaction was also run without the aflatoxin oxime. TLC of the products (using $CHCl_3$:MeOH:$CH_3CO_2H$, 40:10:3) showed many spots. One spot at Rf ~0.7 was found to be absent in the TLC run of the control. This tracer was collected, dissolved in MeOH, and then diluted in buffer so as to give an intensity of ~400,000 relative fluorescence units when 10 µl of this tracer solution was added to 1 of buffer.

It was observed that this tracer gave a stable polarization of ~40 mP. After adding 10 µl of 1/50 diluted antibody (Sigma, A-9555) to give a final dilution of 1/5,000, the polarization slowly increased to ~230 mP is a period of five minutes.

In order to confirm the reactivity, 1 ml buffer was taken and mixed with 10 µl of antibody and 10 µl of (0.8 mg/ml) Aflatoxin $B_1$. The mixture was kept at room temperature for five minutes and then blanked in the FP instrument. After 10 µl of tracer was added, the fluorescence polarization decreased from ~230 mP to ~41 mp.

A different Aflatoxin $B_1$ tracer was prepared using a similar reaction but with fluoresceinamine (isomer 1) as the fluorophore. The resulting tracer showed less sensitivity than when fluoresceinamine (isomer 2) was used as the fluorophore. Specifically, the staring polarization (~32 mP) changes to only ~140 mP when the antibody was added.

Aflatoxin $B_1$ tracers were also prepared using other amine derivatives of fluorescein as the fluorophore. The results are summarized as follows. When 5-aminoacetyl-amidofluorescein (5AFF) was used, the resulting tracer had a fluorescence polarization of ~30 mP, which increased to ~65 mP when antibody was added. When 5-(5-aminopentyl)-thioureidyl fluorescein (5,5APTF) was tried as the fluorophore, the tracer had a fluorescence polarization of ~35 mP, which increased to ~102 mP upon antibody addition. Fluorescein thiosemicarbazide (FTSC), 4-aminomethyl fluorescein, and 5-aminomethyl fluorescein were also tried, but these fluorophores did not result in any active product, i.e., they showed no significant change in fluorescence polarization upon binding to antibody. Therefore, it was concluded from these studies that isomer 2 of fluoresceinamine gave the best results for this antibody.

3. Assay Development

Aflatoxin antibody was purchased from Sigma (A-9555) and used for initial assay development after diluting it (1/150,000) in PBSA-BGG (pH ~7.5), which is a phosphate buffer solution containing 1 gram per liter sodium azide and 9 grams per liter sodium chloride, with bovine gamma globulin (BGG) present at a concentration of 100 µl/ml. 1 ml of the antibody solution was mixed with 50 µl of a solution having a known concentration of free Aflatoxin $B_1$ in methanol/water (70/30). Aflatoxin $B_1$ concentrations varying from 0 to 40 ppb were used: After taking a blank measurement, 10 µl of diluted tracer, prepared as described using fluoresceinamine (isomer 2) as the fluorophore, was added, and the change in fluorescence polarization was monitored for 10 minutes. The results are shown in FIG. 1.

Since aflatoxins are typically extracted from agricultural samples using a mixture of an organic solvent and water, the effect of methanol on the Aflatoxin antibody from Sigma (A-9555) was studied. Specifically, 1 ml of diluted antibody solution was mixed with a known concentration of methanol. After measuring a blank, tracer was added (the Aflatoxin $B_1$ oxime-isomer 2 fluoresceinamine tracer described above), and the fluorescence polarization was measured over time. The results are summarized in Table 1 below and in FIG. 2.

TABLE 1

| Time (Minutes) | 50 ml MeOH | 40 ml MeOH | 30 ml MeOH | 20 ml MeOH | 10 ml MeOH | 50 ml water |
|---|---|---|---|---|---|---|
| 0.5 | 32.0 | 49.70 | 88.80 | 56.70 | 73.20 | 46.30 |
| 1.0 | 91.0 | 105.40 | 74.40 | 117.60 | 128.40 | 129.80 |
| 1.5 | 117.0 | 126.20 | 126.30 | 143.00 | 156.70 | 165.40 |
| 2.0 | 145.9 | 140.50 | 139.30 | 157.70 | 170.40 | 178.60 |
| 2.5 | 150.4 | 152.50 | 154.30 | 168.90 | 179.20 | 188.30 |
| 3.0 | 161.3 | 161.50 | 167.50 | 176.70 | 186.80 | 194.30 |
| 3.5 | 165.5 | 165.70 | 170.30 | 181.90 | 192.10 | 199.60 |
| 4.0 | 168.1 | 175.40 | 178.60 | 186.10 | 195.50 | 202.30 |
| 4.5 | 179.6 | 177.10 | 185.10 | 191.30 | 198.70 | 205.40 |
| 5.0 | 189.3 | 179.10 | 186.80 | 195.50 | 202.10 | 208.30 |
| 5.5 | 186.1 | 185.80 | 187.10 | 198.40 | 204.50 | 209.80 |
| 6.0 | 186.6 | 187.00 | 190.40 | 198.00 | 205.60 | 210.60 |

These results show that the fluorescence polarization decreases as the methanol concentration increases, and, for a given methanol concentration, the fluorescence polarization increases over time. Thus, although the tracer itself is stable in methanol and related organic solvents for an extended period of time, these results suggest that this antibody is sensitive to methanol. As a result, while this antibody has the sensitivity for use in a fluorescence polarization-based assay for aflatoxins, it is preferable to use an antibody that is more stable in methanol in order to yield more reliable results. It was found that the monoclonal antibody available from Dr. Chris Maragos of the Agricultural Research Unit of the United States Department of Agriculture (Peoria, Ill.) had the desired stability in methanol.

4. FP Assay for Aflatoxins in Naturally Contaminated Corn Samples

Corn samples that were naturally contaminated with aflatoxins were purchased from Trilogy Analytical Laboratory, Inc. (Washington, Mo.). Aflatoxin was extracted from each 20 g sample of crushed grain using 100 ml mixture of MeOH/water (70/30) in duplicate by shaking each sample from time to time for about 30 minutes. Extracts were filtered through a fine filter paper and stored in sealed bottles at room temperature for analysis.

Figure 3:
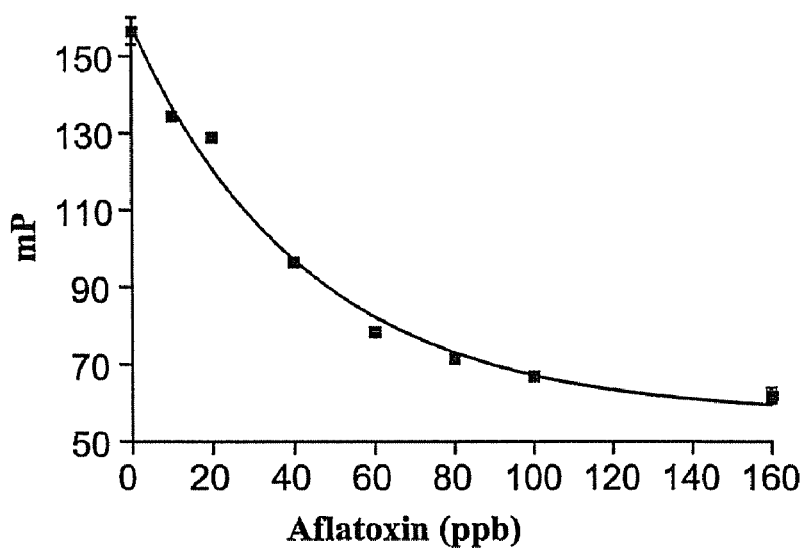
FIG. 3 is a standard curve for a fluorescence polarization assay for aflatoxins, using the data Table 2, in accordance with an embodiment of the present invention.

Standards were prepared in MeOH/water (70/30) by diluting a concentrate of Aflatoxin $B_1/B_2/G_1/G_2$ (7/1/3/1) provided by Trilogy into various concentrations. 40 μl of each sample or standard was mixed into 1 ml antibody solution (1/150,000 in PBSA-BGG buffer) in a test tube. The antibody used was the methanol resistant antibody provided by Dr. Chris Maragos. After blanking each sample, 10 μl of tracer was added into each tube, the samples were incubated for 15 minutes at room temperature, and then the fluorescence polarization was measure for each tube. The tracer that was used was the Aflatoxin $B_1$ oxime-isomer 2 fluoresceinamine tracer described above. A standard curve was plotted using duplicate values. The fluorescence polarization values for the standards are shown below in Table 2 and in FIG. 3.

TABLE 2

| Aflatoxin Concentration (ppb) | mP (first run) | mP (second run) |
|---|---|---|
| 0.0 | 153.0 | 160.0 |
| 10.0 | 134.0 | 135.0 |
| 20.0 | 128.0 | 130.0 |
| 40.0 | 97.0 | 96.0 |
| 60.0 | 78.0 | 79.0 |
| 80.0 | 71.0 | 72.0 |
| 100.0 | 67.0 | 67.0 |
| 160.0 | 64.0 | 60.0 |

The concentration of aflatoxin in each corn sample was then calculated from the standard curve. The results are summarized in Table 3 below.

TABLE 3

| Sample | mP (first run) | mP (second run) | Calculated aflatoxin concentration (ppb) |
|---|---|---|---|
| 1 | 163.0 | 159.0 | 0 |
| 2 | 143.5 | 135.0 | 8.99 |
| 3 | 80.0 | 75.5 | 69 |
| 4 | 92.0 | 90.5 | 47 |
| 5 | 98.0 | 112.5 | 32.61 |
| 9 | 73.5 | 76.5 | 75.16 |
| 7 | 75.5 | 71.0 | 79.94 |
| 8 | 83.0 | 87.0 | 56 |
| 10 | 125.0 | 124.5 | 17.35 |
| 11 | 146.5 | 146.0 | 5.4 |

Figure 4:
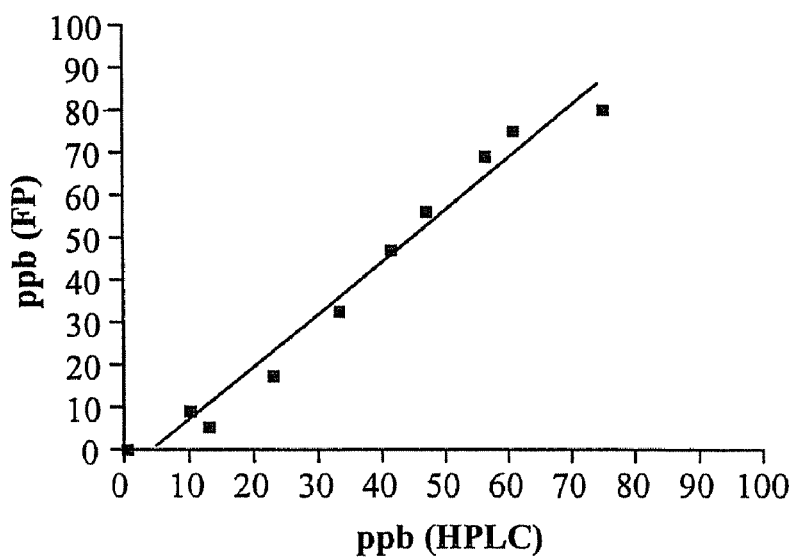
FIG. 4 is a graph comparing the aflatoxin concentration of samples as measured using HPLC with the aflatoxin concentration as calculated from the standard curve of FIG. 3, in accordance with an embodiment of the present invention.

These samples were also analyzed using both the fluorescence polarization protocol described above and by standard HPLC techniques, and the aflatoxin concentrations determined using these two techniques were compared. The results are summarized below in Table 4 and FIG. 4, except for the results from one sample that had a very high level of aflatoxin contamination. These results show a good correlation between HPLC and FP ($r^2=0.97$).

TABLE 4

| Aflatoxin concentration from HPLC (ppb) | Aflatoxin concentration from FP (ppb) |
|---|---|
| 0.50 | 0.0 |
| 10.20 | 9.0 |
| 56.40 | 69.0 |
| 41.50 | 47.0 |
| 33.30 | 32.6 |
| 47.10 | 56.0 |
| 60.80 | 75.0 |
| 75.00 | 80.0 |
| 13.01 | 5.4 |

Figure 5:
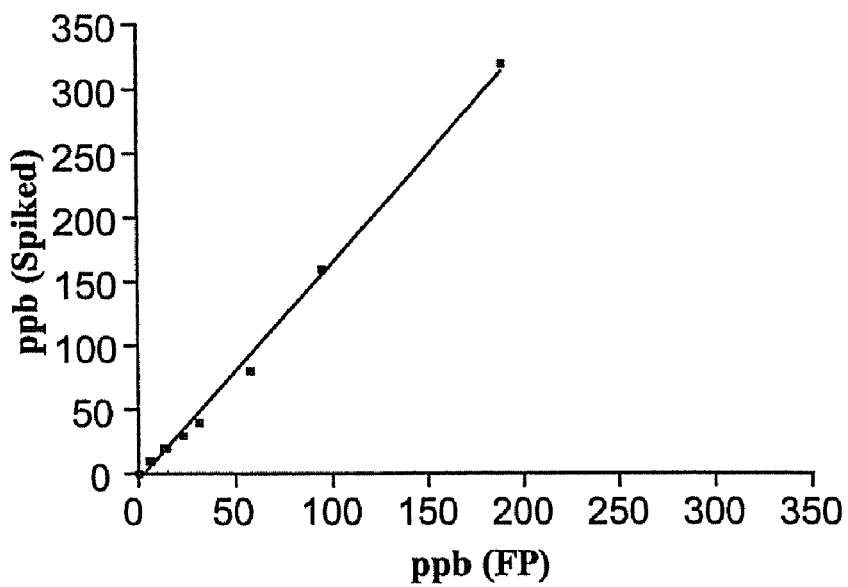
FIG. 5 is graph comparing the aflatoxin concentration of spiked samples with the aflatoxin concentration calculated from measurements of fluorescence polarization, in accordance with an embodiments of the present invention.

5. Analysis Aflatoxin in Popcorn Samples 20 g of crushed samples of aflatoxin-free were spiked with an Aflatoxin $B_1/B_2/G_1/G_2$ mixture (7/1/3/1) to a known concentration. The fluorescence polarization analysis was performed in duplicate on each extract as reported above. The aflatoxin concentration of each sample was calculated from the average measures fluorescence polarization, using a calibration curve, and compared with the known spiked concentration. The results are summarized in Table 5 below and in FIG. 5. In this study, the sample spiked to 320 ppb was diluted 1/10 for the fluorescence polarization measurement.

TABLE 5

| Spiked Aflatoxin Concentration (ppb) | mP | Calculated Aflatoxin Concentration (ppb) |
|---|---|---|
| 0 | 178 | 0.47 |
| 10 | 169 | 5.79 |
| 10 | 168 | 6.43 |
| 20 | 157 | 14.60 |
| 20 | 159 | 13.16 |
| 30 | 148 | 23.30 |
| 40 | 142 | 31.12 |
| 80 | 129 | 57.72 |
| 160 | 122 | 94.74 |
| 320 | 152 | 189 |

These results show a good correlation between theoretical values and the results obtained using the fluorescence polarization assay of the present invention ($r^2=0.0996$). However, the fluorescence polarization results consistently underestimated the actual aflatoxin concentration. One explanation is that naturally contaminated samples had mainly $B_1$ and some $B_2$, but no $G_1$ and $G_2$, whereas the popcorn samples were spiked with a mixture of $B_1/B_2/G_1/G_2$ in a 7/1/3/1 ratio.

Figure 6:
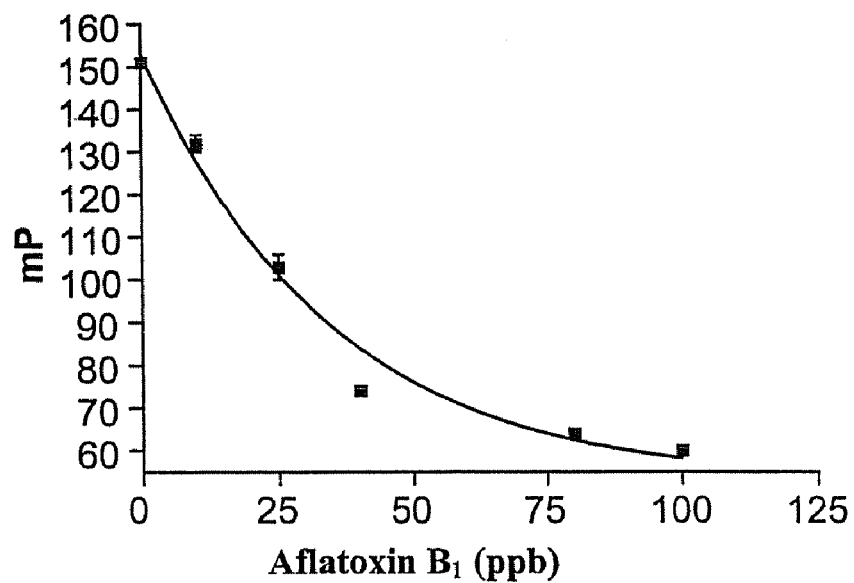
FIG. 6 is a standard curve for a fluorescence polarization assay for aflatoxins, used to obtain the data in Tables 6 and 7, in accordance with an embodiment of the present invention.

To test this explanation, the cross-reactivity of these aflatoxins was investigated. Aflatoxin $B_1$, $B_2$, $G_1$ and $G_2$ were purchased from Sigma and individually diluted in a mixture of methanol/water (70/30) to give a range of concentrations, namely, 10, 25, 40, 80, and 100 ppb. The standard curve shown in FIG. 6 was obtained by performing the fluorescence polarization assay described herein on the Aflatoxin $B_1$ solutions. Table 6 and Table 7 show the results for Aflatoxin $G_1$ and $G_2$, respectively, calculating the aflatoxin concentrations from the calibration curve of FIG. 6.

TABLE 6

| Aflatoxin $G_1$ Concentration (ppb) | mP | Calculated Aflatoxin Concentration (ppb) |
|---|---|---|
| 10 | 143 | 3.75 |
| 25 | 130 | 9.06 |
| 40 | 115 | 16.44 |
| 80 | 101 | 25.16 |
| 100 | 99 | 26.61 |

TABLE 7

| Aflatoxin $G_2$ Concentration (ppb) | mP | Calculated Aflatoxin Concentration (ppb) |
|---|---|---|
| 10 | 144 | 3.37 |
| 25 | 133 | 7.76 |
| 40 | 113 | 17.56 |
| 80 | 101 | 25.16 |
| 100 | 98 | 27.35 |

These results show that the concentration of Aflatoxin $G_1$ and $G_2$ are underestimated when they are calculated from a calibration curve obtained from Aflatoxin $B_1$ alone. More particularity, Aflatoxin $G_1$ and $G_2$ both cross-react with Aflatoxin $B_1$ only to the extent of 30-40%. This may explain the underestimation of aflatoxin concentration observed in the spiked popcorn samples.

6. Assay Kit

The material used to perform the assay of the present invention are preferably made available in kit form. The kit preferably includes a quantity of extraction solution for extracting aflatoxin from samples of grain or other products, tracer and antibody in an amount suitable for at least one assay, along with suitable packaging and instructions for use. The tracer and antibody may be provided in solution, as a liquid dispersion, or as a substantially dry powder (e.g., in lyophilized form).

The suitable packaging can be any solid matrix or material, such as glass, plastic, paper, foil, and the like, capable of separately holding within fixed limits the buffer, tracer, and antibody. For example, the extraction solvent, tracer, and monoclonal antibody may be provided as solutions in separate labeled bottles or vials made of glass or plastic.

The antibody is specific for aflatoxins and is preferably monoclonal antibody. Most preferably, the monoclonal antibody is stable in the extraction solvent.

The tracer comprises a fluorophore conjugated to an aflatoxin oxime, preferably (Aflatoxin $B_1$)-O-carboxymethyloxime. Suitable fluorophores include fluoresceinamine (isomer 1), fluoresceinamine (isomer 2), 5-aminoacetyl-amidofluorescein (5AAF), 5-(5-aminopentyl)-thioureidyl fluorescein (5,5APTF). Other fluorophores may be used, provided the resulting tracer is able to bind with the antibody to produce a detectable change in fluorescence polarization. Preferably the fluorophore is fluoresceinamine. Most preferably, the fluorophore is fluoresceinamine (isomer 2).

The extraction solvent is preferably a mixture of an organic solvent, such as methanol or acetonitrile, in water. Most preferably, the extraction solvent is a methanol/water (70/30) mixture.

7. References (1) Langone, J. J.; Vunakis, H. V. "Aflatoxin B1: Specific antibodies and their use in radioimmunoassays." *J. Natl. Cancer Inst.* 1976, 56, 591-595.

(2) Sizaret, P.; Malaveille, C.; Montesano, R.; Frayssinet, C. "Detection of Aflatoxins and related metabolites by radio-immunoassay." *J. Natl. Cancer Inst.* 1982, 69, 1375-1381.

(4) Wilson, T. J.; Romer, T. R. "Mycotoxins: Use of the mycosep multifunctional cleanup column for liquid chromatographic determination of Aflatoxins in agricultural products." *J. Assoc. Off Anal. Chem.* 1991, 74, 951956.

(5) Newberne, P. M.; Butler, W. H. *Cancer Res.* 1969, 29, 236_250.

(6) Trucksess, M. W.; Stack, M. E.; Nesheim, S.; Page, S. W.; Albert, R. H.; Hansen, T. J.; Donahue, K. F. "Immunoaffinity column couples with solution fluorometry or liquid chromatography postcolumn derivatization for determination of aflatoxins in corn, peanuts and peanut butter: Collaborative study" *J. Assoc. Off. Anal. Chem.* 1991, 74, 81-88.

(7) Wild, C. P.; Pionneau, F. A.; Montesano, R.; Mutiro, C. F.; Chetsanga, C. J. "Aflatoxin detection in human breast milk by immunoassay." *Int. J. Cancer.* 1987, 40, 328-333.

(8) Trucksess, M. W.; Stack, M. E.; Nesheim, S.; Albert, R. H.; Romer, T. R. "Multifunctional column couples with liquid chromatography for determination of aflatoxins B1, B2, G1 and G2 in corn, almonds, brazil nuts, peanuts and pistachio nuts: Collaborative study." *J. AOAC. Int.* 1994, 77, 1515-1521.

(9) Campbell, T. C.; Stoloff, L. "Implication of mycotoxins for human health." *J. Agr. Food Chem.* 1974, 22, 1006-1014.

(10) Seitz, L. M. "Comparison of methods of aflatoxin analysis by high-pressure liquid chromatography." *J. Chromatogr.* 1975, 104, 81-91.

(11) Asao, T.; Buchi, G.; Abdel-kader, M. M.; Chang, S. B.; Wick, E. L.; Wogan, G. N. "The structure of Aflatoxins B and $G_1$." *J. Am. Chem. Soc.* 1965, 87, 882-886.

What is claimed is:

1. A homogeneous assay for the determination of aflatoxins in agricultural products, said homogeneous assay comprising the steps of:
    combining an aflatoxin extract with a tracer and an antibody to provide a mixture, said antibody being specific for aflatoxin, said tracer comprising an aflatoxin oxime conjugated to isomer 2 of fluoresceinamine, said tracer being able to bind to said antibody to produce a detectable change in fluorescence polarization;
    measuring the fluorescence polarization of said mixture to obtain a measured fluorescence polarization; and
    comparing said measured fluorescence polarization with a characterized fluorescence polarization value, said characterized fluorescence polarization value corresponding to a known aflatoxin concentration.

2. The assay of claim 1, further comprising providing the aflatoxin extract by a process comprising the steps of:
    obtaining a sample of an agricultural product;
    crushing said sample to provide a crushed sample; and
    shaking said crushed sample with an extraction solvent for a predetermined time.

3. The assay of claim 2, wherein said extraction solvent comprises an organic solvent and water.

4. The assay of claim 3, wherein said organic solvent is methanol.

5. The assay of claim 1, wherein said aflatoxin oxime is (Aflatoxin $B_1$)-O-carboxymethyloxime.

6. The assay of claim 1, further comprising the steps of:
providing a plurality of aflatoxin standard solutions, each of said aflatoxin standard solutions having a different known concentration of aflatoxin;
adding said tracer and said antibody to each one of said plurality of aflatoxin standard solutions, so as to provide a plurality of standard mixtures; and
measuring the fluorescence polarization of each one of said plurality of said standard mixtures to provide a plurality of standard fluorescence polarization values corresponding to known aflatoxin concentrations.

7. The assay of claim 6, wherein said characterized fluorescence polarization value is one of said standard fluorescence polarization values.

8. An assay kit for the determination of aflatoxins in agricultural products using a homogeneous assay, said assay kit comprising:
an extraction solvent for extracting aflatoxin from a sample, said extraction solvent comprising an organic solvent;
an antibody and a tracer, each in an amount suitable for at least one assay, and suitable packaging, said antibody being specific for aflatoxin, said tracer comprising an aflatoxin oxime conjugated to isomer 2 of fluoresceinamine, said tracer being able to bind to said antibody to produce a detectable change in fluorescence polarization, said antibody being stable in said extraction solvent during said homogeneous assay.

9. The assay kit of claim 8, wherein said organic solvent is methanol.

10. The assay kit of claim 8, wherein said aflatoxin oxime is (Aflatoxin $B_1$)-O-carboxymethyloxime.

11. The assay of claim 3, wherein said antibody is stable in said extraction solvent.

12. A homogeneous assay for the determination of aflatoxins in agricultural products, said homogeneous assay comprising the steps of:
extracting aflatoxin from a sample into an extraction solvent to provide an aflatoxin extract, wherein said extraction solvent comprises an organic solvent;
combining said aflatoxin extract with a tracer and an antibody to provide a mixture, said antibody being specific for aflatoxin, said tracer comprising an aflatoxin oxime conjugated to isomer 2 of fluoresceinamine, said tracer being able to bind to said antibody to produce a detectable change in fluorescence polarization;
incubating said mixture for an incubation period, wherein said antibody is stable in said extraction solvent during said incubation period;
after said incubation period, measuring the fluorescence polarization of said mixture to obtain a measured fluorescence polarization; and
comparing said measured fluorescence polarization with a characterized fluorescence polarization value, said characterized fluorescence polarization value corresponding to a known aflatoxin concentration.

13. The assay of claim 12, wherein said organic solvent is methanol.

14. The assay of claim 12, wherein said incubation period is 15 minutes.

15. The assay of claim 12, wherein said aflatoxin oxime is (Aflatoxin $B_1$)-O-carboxymethyloxime.

16. The assay of claim 12, wherein said incubation period is at least 5 minutes.

* * * * *